United States Patent [19]

Hoegerle et al.

[11] Patent Number: 4,686,294

[45] Date of Patent: Aug. 11, 1987

[54] 1,3,4-THIADIAZOLYL UREAS AND PROCESSES FOR CONTROLLING WEEDS AND WILD GRASSES THEREWITH

[75] Inventors: Karl Hoegerle, Basel; Hans J. Cellarius, Riehen; Paul Rathgeb, Basel; Jürg Rumpf, Binningen, all of Switzerland

[73] Assignee: Ciba-Geigy Corporation, Ardsley, N.Y.

[21] Appl. No.: 785,762

[22] Filed: Dec. 20, 1968

[51] Int. Cl.$^4$ ............................................. C07D 285/12
[52] U.S. Cl. ........................................ 548/140; 71/90
[58] Field of Search .................. 260/306.8 D; 548/140

[56] References Cited

U.S. PATENT DOCUMENTS 3,288,851  11/1966  Martin et al. ........................ 71/119
3,304,167   2/1967  Buntin et al. ........................ 71/119

*Primary Examiner*—Glennon H. Hollrah
*Assistant Examiner*—D. I. Dinner

*Attorney, Agent, or Firm*—Edward McC. Roberts; Frederick H. Rabin

[57] ABSTRACT

Compounds of the formula

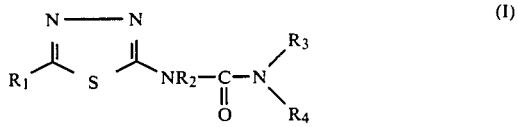

are described in which $R_1$ represents a perfluoroalkyl radical of from 1 to 2 carbon atoms, and at least one of $R_2$ and $R_3$ represents hydrogen, and the other, or both represent lower alkyl, and $R_4$ represents a lower alkyl radical which may be unsubstituted or bear certain substitution, and which are useful as herbicides in a method for controlling weeds and wild grasses. Compositions containing such compounds are also described. Finally, novel fluoro-thio semicarbazides are described which are useful intermediates in the production of the compounds of Formula I.

1 Claim, No Drawings

1,3,4-THIADIAZOLYL UREAS AND PROCESSES FOR CONTROLLING WEEDS AND WILD GRASSES THEREWITH

The present invention concerns new 1,3,4-thiadiazolyl ureas, processes for their production, herbicidal compositions, which contain such ureas as active substances, and a method for controlling weeds and wild grasses with the aid of the new active substances or compositions which contain them.

This invention thus provides new 1,3,4-thiadiazolyl ureas which correspond to the formula $$\underset{R_1}{\overset{N-\!\!-\!\!N}{\underset{S}{\bigvee}}}NR_2-\underset{\overset{\|}{O}}{C}-N\overset{R_3}{\underset{R_4}{\diagdown}} \quad (I)$$

wherein $R_1$ represents a perfluoroalkyl radical of from 1 to 2 carbon atoms, $R_2$ represents hydrogen or a lower alkyl radical, $R_3$ represents hydrogen or a lower alkyl radical with the proviso that at least one of the symbols $R_2$ and $R_3$ represents hydrogen, and $R_4$ represents a lower alkyl radical any substituent of which is selected from chlorine, bromine, cyano, lower alkoxy or lower alkylthio; an alkenyl or alkinyl radical having 3 or 4 carbon atoms, a cycloalkyl radical having 3 to 6 carbon atoms, or a lower alkoxy radical.

In Formula I in the definition of $R_1$, the perfluoroalkyl radical denotes preferably the trifluoromethyl radical. Suitable as lower alkyl radicals $R_2$, $R_3$ and $R_4$ are straight- or branched-chain radicals having 1 to 4 carbon atoms, preferably the methyl and the ethyl radicals.

The new 1,3,4-thiadiazolyl ureas of Formula I are produced according to the invention by reacting a 2-amino-1,3,4-thiadiazole of the formula $$\underset{R_1}{\overset{N-\!\!-\!\!N}{\underset{S}{\bigvee}}}NH-R_2 \quad (II)$$

wherein $R_1$ and $R_2$ have the meanings given under Formula I, with a halogen carbonic acid ester in the presence of an acid-binding agent to form the carbamic acid derivative and reacting the latter with an amine of the formula $$HN\overset{R_3}{\underset{R_4}{\diagdown}} \quad (III)$$

wherein $R_3$ and $R_4$ have the meanings given under Formula I.

The new 1,3,4-thiadiazolyl ureas of the formula $$\underset{R_1}{\overset{N-\!\!-\!\!N}{\underset{S}{\bigvee}}}NR_2-\underset{\overset{\|}{O}}{C}-N\overset{H}{\underset{R_4'}{\diagdown}} \quad (Ia)$$

wherein $R_1$ represents a perfluoroalkyl radical with 1 or 2 carbon atoms, $R_2$ represents hydrogen or a lower radical, and $R_4'$ represents a lower alkyl radical any substituent of which is selected from chlorine, bromine, lower alkoxy or lower alkylthio; or a cycloalkyl radical with 3 to 6 carbon atoms, can also be produced according to the invention by reacting a 2-amino-1,3,4-thiadiazole of the formula II:

$$\underset{R_1}{\overset{N-\!\!-\!\!N}{\underset{S}{\bigvee}}}NH-R_2 \quad (II)$$

wherein $R_1$ and $R_2$ have the meanings given under formula Ia, with an isocyanate of the formula IV:

$$R_4'-NCO \quad (IV)$$

wherein $R_4'$ has the meanings given under formula Ia.

As halogen carbonic acid esters preferably phenyl chlorocarbonate or phenyl chlorothiocarbonate are used. As amines of the formula III the following, for example, can be used:

Methylamine, dimethylamine, ethylamine, diethylamine, isopropylamine, n-butylamine, sec.-butylamine, cyclopropylamine, cyclopentylamine, cyclohexylamine, N-methyl-N-cyclohexylamine, 1-cyano-1-methylethyl-amine, 2-chloroethylamine, 2-bromoethylamine, 2-methoxyethylamine, 2-ethoxyethylamine, 2-methylthioethylamine, allylamine, methylallylamine, N-methyl-N-allylamine, N-methyl-N-1'-methylpropargylamine, O-methylhydroxylamine, O,N-dimethylhydroxylamine.

Tertiary amines are preferably used as acid-binding agents, e.g. trialkyl amines, pyridine bases, etc., also inorganic bases, such as hydroxides and carbonates of alkali and alkaline earth metals. The reaction temperatures lie in each case between 0° and 150° C.

The reaction of the resultant intermediate carbamic acid derivatives with a primary or secondary amine of the formula 1a III and the reaction of a 2-amino-1,3,4-thiadiazole of the formula II with an isocyanate of the formula IV are performed at temperatures between −40 and 150° C., preferably between 0° and 100° C. The thiadiazolyl ureas according to the invention are obtained in good yields and high purity. The new compounds are stable and soluble in the usual organic solvents, but have low solubility in water.

The processes described are carried out in the presence of solvents or diluents which are inert to the reactants. For example, the following can be used:

Aliphatic and aromatic hydrocarbons and halogenohydrocarbons, such as benzene, toluene, xylenes, chloroform, chlorinated ethylene; N,N-dialkylated amides, such as dialkyl formamides; dialkyl ethers and ether derivatives; higher ketones, such as methylethyl ketone, nitriles, etc.

In addition, the new 1,3,4-thiadiazolyl ureas can be obtained by reacting a 2-amino-1,3,4-thiadiazole of the formula II wherein $R_2$ represents hydrogen, with a carbamoyl halide of the formula

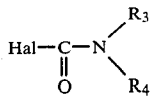

wherein $R_3$ represents lower alkyl, in the presence of acid-binding agents.

In a further procedure, the new compounds of the formula I can be obtained by converting a 2-amino-1,3,4-thiadiazole of the formula II with phosgene into the thiadiazolyl carbamoyl chloride, and then reacting the latter, which, in case $R_2$ represents hydrogen, is present in equilibrium with the isocyanate, with an amine of the formula III.

Of the 2-amino-1,3,4-thiadiazoles of formula II used as starting compounds, the 2-amino-5-trifluoromethyl-thiadiazole was hitherto known [J. Lalezari et al., J. heterocycl. Chem. 3. 336–337 (1966)]. The new 2-amino-thiadiazoles of formula II can be obtained from corresponding fluoroacyl thiosemicarbazides by ring-closure reaction with polyphosphoric acid in accordance with the process described by E. Hoggarth in J. chem. Soc. 1949, 1163–1167. Fluoroacyl thiosemicarbazides have not been known hitherto. They are obtained by reacting equimolar amounts of a corresponding aliphatic fluorocarboxylic acid derivative, particularly the anhydride, with a thiosemicarbazide in the presence of a solvent or diluent. 4-Alkylthiosemicarbazides are known compounds. To obtain 1,3,4-thiadiazoles, the fluoroacyl thiosemicarbazides can be used as such or produced in situ.

As fluoroacylthiosemicarbazides the following, for example, can be used:
1-trifluoroacetylthiosemicarbazide,
1-trifluoroacetyl-4-methylthiosemicarbazide,
1-trifluoroacetyl-4-ethylthiosemicarbazide,
1-trifluoroacetyl-4-isopropyl-thiosemicarbazide,
1-trifluoroacetyl-4-n-butyl-thiosemicarbazide,
1-pentafluoropropionylthiosemicarbazide.

The new 1,3,4-thiadiazolyl ureas of the formula I possess excellent herbicidal properties and can be used in concentrations of from 0.1 to 35 kg per hectare for controlling mono- and dicotyl weeds and wild forms of grass. In high concentrations, the new ureas act as total herbicides, and in lower concentrations, i.e., of from 0.1 to 5 kg per hectare, they act as selective herbicides. Deep rooted types of weeds and those more difficult to control, e.g. leguminosae and umbelliferous plants are attacked by these active substances. They can be applied equally successfully both as pre-emergence and post-emergence agents. It is thus possible to destroy or prevent field weeds such as, e.g. Panicum sp., Sinapis sp., Chenepodiaceae, Alopercurus sp., Matricaria sp., without causing damage to cultivated plants, such as corn etc.

The new 1,3,4-thiadiazolyl ureas of the formula I are used, mixed with usual additives, as herbicidal compositions. Moreover, the new active substances can also be mixed with fertilizers and applied in this form. In order to broaden the range of activity of the ureas according to the invention, they can be applied in admixture with other herbicides: e.g. with halogen-, alkoxy- and alkylthio-diamino-s-triazines; halogenated phenols, nitrophenols, aliphatic, aromatic and araliphatic carboxylic acids as well as with the salts of such compounds; ureas, carbamic acid esters, uracils, inorganic salts, etc., such as:
2-chloro-4,6-bis-(ethylamino)-s-triazine,
2-chloro-4-ethylamino-6-isopropylamino-s-triazine,
2-chloro-4,6-bis-(methoxypropylamino)-s-triazine,
2-methoxy-4,6bis-(isopropylamino)-s-triazine,
2-diethylamino-4-isopropylacetamido-6-methoxy-s-triazine,
2-isopropylamino-4-methoxypropylamino-6-methyl-mercapto-s-triazine,
2-methylmercapto-4,6-bis-(isopropylamino)-s-triazine,
2-methylmercapto-4,6-bis-(ethylamino)-s-triazine,
2-methylmercapto-4-ethylamino-6-isopropylamino-s-triazine,
2-methoxy-4,6-bis-(ethylamino)-s-triazine,
2-methoxy-4-ethylamino-6-isopropylamino-s-triazine,
2-chloro-4,6-bis-(isopropylamino)-s-triazine,
dinitro-sec.-sec.-butyl phenol and salts thereof,
pentachlorophenol and salts thereof,
2,3,6-trichlorobenzoic acid and salts thereof,
2,3,5,6-tetrachlorobenzoic acid and salts thereof,
2-methoxy-3,5,6-trichlorobenzoic acid and salts thereof,
2-methoxy-3,6-dichlorobenzoic acid and salts thereof,
3-amino-2,5-dichlorobenzoic acid and salts thereof,
3-nitro-2,5-dichlorobenzoic acid and salts thereof,
2-methyl-3,6-dichlorobenzoic acid and salts thereof,
2,4-dichlorophenoxyacetic acid and salts and esters thereof,
2,4,5-trichlorophenoxyacetic acid and salts and esters thereof,
(2-methyl-4-chlorophenoxy)-acetic acid and salts and esters thereof,
2-(2,4,5-trichlorophenoxy)-propionic acid and salts and esters thereof,
2-(2,4,5-trichlorophenoxy)-ethyl-2,2-dichloropropionic acid esters,
4-(2,4-dichlorophenoxy)-butyric acid and salts and esters thereof,
4-(2-methyl-4-chlorophenoxy)-butyric acid and salts and esters thereof,
2,3,6-trichlorobenzyloxypropanol,
2,6-dichlorobenzonitrile, trichloroacetic acid and salts thereof,
2,2-dichloropropionic acid and salts thereof,
2,3,6-trichlorophenyl-acetic acid and salts thereof,
2-chloro-N,N-diallyl-acetamide,
3-(3,4-dichlorophenyl)-1,1-dimethyl-urea,
3-(4-chlorophenyl)-1,1-dimethyl-urea,
3-phenyl-1,1-dimethyl-urea,
3-(3,4-dichlorophenyl)-3-methoxy-1,1-dimethyl-urea,
3-(3,4-dichlorophenyl)-1-n-butyl-1-methyl-urea,
3-(3,4-dichlorophenyl)-1-methoxy-1-methyl-urea,
3-(4-chlorophenyl)-1-methoxy-1-methyl-urea,
3-(3,4-dichlorophenyl)-1,1,3-trimethyl-urea,
3-(3,4-dichlorophenyl)-1,1-diethyl-urea,
3-(4-chlorophenoxyphenyl)-1,1-dimethyl-urea,
N,N-Di-(n-propyl)-O-ethyl thiocarbamate,
N,N-Di-(n-propyl)-O-n-propyl thiocarbamate,
N-ethyl-N-(n-butyl)-O-ethyl thiocarbamate,
N-ethyl-N-(n-butyl)-O-n-propyl thiocarbamate,
N-phenyl-O-isopropyl carbamate,
N-(m-chlorophenyl)-O-isopropyl carbamate, N-(m-chlorophenyl)-O-4-chloro-2-butyryl carbamate, maleic hydrazide.

The term "lower" used in connection with an aliphatic radical such as an alkyl, alkoxy or alkylthio group means that such group has at most 4 carbon atoms.

The following examples describe the production of new 1,3,4-thiadiazolyl ureas of the formula I. The temperatures are given in degrees centigrade.

EXAMPLE 1

(a) A mixture of 91.1 g of thiosemicarbazide and 125 g of trifluoroacetic acid in a sulphonating flask is heated to reflux temperature (72°). 1 kg of polyphosphoric acid is then added cautiously with stirring.

The reaction mixture is kept at the reflux temperature of trifluoroacetic acid until all of the latter is bound. The reaction mixture is then slowly heated to 130°, and, after keeping it for 1 hour at this temperature, cooled to 80°. The mixture is poured into about 3 l of ice water and the reaction product precipitated by adding concentrated sodium hydroxide solution (until pH 5–6). The crude product is recrystallised from aqueous ethanol. The 2-amino-5-trifluoromethyl-1,3,4-thiadiazole thus obtained melts at 212°–214°.

(b) To the solution of 6.75 g of 2-amino-5-trifluoromethyl-1,3,4-thiadiazole in 10 ml of dimethyl formamide at about 50°–60°, 2.8 ml of methyl isocyanate are added. Following completion of the reaction, the N-[5-trifluoromethyl-1,3,4-thiadiazolyl(2)]-N'-methyl urea separates in crystalline form. Melting point 186°–189°.

EXAMPLE 2

(a) 46.8 g of trifluoroacetic acid anhydride are added dropwise at 0° to a suspension of 27.3 g of 4-methyl-thiosemicarbazide in 300 ml of ether. The mixture is then stirred for 8 hours at room temperature. After cooling, the reaction product is separated and washed with a little cold ether. The 1-trifluoroacetyl-4-methyl-thiosemicarbazide thus obtained melts at 163°–164°.

(b) 25 g of 1-trifluroacetyl-4-methyl-thiosemicarbazide are introduced in portions within 15 minutes into 125 g of polyphosphoric acid at 80°. The reaction mixture is then heated to 120° and stirred for about 30 minutes at this temperature. The reaction mixture, previously cooled to about 70°, is then poured into 500 ml of ice-water, and the product is precipitated by adding aqueous concentrated ammonia solution, separated and washed with water. After recrystallising from ethanol/water, the 2-methylamino-5-trifluoromethyl-1,3,4-thiadiazole has a melting point of 115°–116°.

(c) 12 g of 2-methylamino-5-trifluoromethyl-1,3,4-thiadiazole are dissolved at about 50°–60° in 30 ml of dimethyl formamide, and 4 g of methyl isocyanate are then added. Following completion of the reaction, the N-[5-trifluoromethyl-1,3,4-thiadiazolyl(2)]-N,N'-dimethyl urea separates in crystalline form. Melting point 134°.

EXAMPLE 3

(a) 31.5 g of phenyl chlorocarbonate are added dropwise at room temperature to a suspension of 34 g of 2-amino-5-trifluoromethyl-1,3,4-thiadiazole in 300 ml of acetonitrile and 20 g of triethylamine. The mixture is stirred for 15 hours at room temperature and subsequently evaporated to dryness in vacuo. The residue is taken up in 100 ml of water and heated for 15 minutes on a steam bath. After cooling, the crystalline precipitate is separated and recrystallised in methanol. The O-phenyl N-[5-trifluoromethyl-1,3,4-thiadiazolyl(2)]-carbamate has a melting point of 180° to 182°.

(b) Gaseous dimethylamine is passed at 80° through the suspension of 14.5 g of O-phenyl N-[5-trifluoromethyl-1,3,4-thiadiazolyl(2)]-carbamate in 300 ml of benzene until the reaction is completed. The course of the reaction is observed by means of thin layer chromatography. The N-[5-trifluoromethyl-1,3,4-thiadiazolyl(2)]-N',N'-dimethyl urea crystallises from the reaction mixture. Melting point 159°–160°.

The same compound is obtained when the S-phenyl thiocarbamate is prepared according to Example 3, (a) and then reacted as described above under (b).

In the manner described in the previous examples, the following 1,3,4-thiadiazolyl ureas are obtained.

TABLE I

| No. | Compound | Melting point |
|---|---|---|
| 1 | N—[5-trifluoromethyl-1,3,4-thiadiazolyl(2)]-N'—ethyl urea | 180–181° |
| 2 | N—[5-trifluoromethyl-1,3,4-thiadiazolyl(2)]-N'—isopropyl urea | 158–161° |
| 3 | N—[5-trifluoromethyl-1,3,4-thiadiazolyl(2)]-N'—n-butyl urea | 152–154° |
| 4 | N—[5-trifluoromethyl-1,3,4-thiadiazolyl(2)]-N'—cyclohexyl urea | 175–177° |
| 5 | N—[5-trifluoromethyl-1,3,4-thiadiazolyl(2)]-N'—cyclopropyl urea | 191–192° |
| 6 | N—[5-trifluoromethyl-1,3,4-thiadiazolyl(2)]-N',N'—diethyl urea | 110–113° |
| 7 | N—[5-trifluoromethyl-1,3,4-thiadiazolyl(2)]-N'—methoxy-N'—methyl urea | 108° |
| 8 | N—[5-trifluoromethyl-1,3,4-thiadiazolyl(2)]-N'—methyl-N'—1'-methylpropargyl urea | 129° |
| 9 | N—[5-trifluoromethyl-1,3,4-thiadiazolyl(2)]-N'—(α-cyano-α-methyl-ethyl)urea | 171° |
| 10 | N—[5-trifluoromethyl-1,3,4-thiadiazolyl(2)]-N'—β-methoxyethyl urea | 169° |
| 11 | N—[5-trifluoromethyl-1,3,4-thiadiazolyl(2)]-N'—β-methylthioethyl urea | 132° |
| 12 | N—[5-trifluoromethyl-1,3,4-thiadiazolyl(2)]-N'—allyl urea | 160° |
| 13 | N—[5-trifluoromethyl-1,3,4-thiadiazolyl(2)]-N'—sec.-butyl urea | 118° |
| 14 | N—[5-trifluoromethyl-1,3,4-thiadiazolyl(2)]-N—methyl-N'—β-chloroethyl urea | 113° |
| 15 | N—[5-trifluoromethyl-1,3,4-thiadiazolyl(2)]-N—methyl-N'—β-methoxyethyl urea | 70° |
| 16 | N—[5-trifluoromethyl-1,3,4-thiadiazolyl(2)]-N—methyl-N'—n-butyl urea | 67° |
| 17 | N—[5-trifluoromethyl-1,3,4-thiadiazolyl(2)]-N—methyl-N'—cyclohexyl urea | 111° |
| 18 | N—[5-trifluoromethyl-1,3,4-thiadiazolyl(2)]-N—methyl -N'—cyclopropyl urea | 111° |
| 19 | N—[5-trifluoromethyl-1,3,4-thiadiazolyl(2)]-N—ethyl-N'—methyl urea | 128° |
| 20 | N—[5-trifluoromethyl-1,3,4-thiadiazolyl(2)]-N—ethyl-N'—isopropyl urea | 99° |
| 21 | N—[5-trifluoromethyl-1,3,4-thiadiazolyl(2)]-N—ethyl-N'—n-butyl urea | 61° |
| 22 | N—[5-trifluoromethyl-1,3,4-thiadiazolyl(2)]-N,N'—diethyl urea | 78° |
| 23 | N—[5-trifluoromethyl-1,3,4-thiadiazolyl(2)]-N'—methyl urea | 157° |
| 24 | N—[5-trifluoromethyl-1,3,4-thiadiazolyl(2)]-N—isopropyl-N'—methyl urea | |
| 25 | N—[5-trifluoromethyl-1,3,4-thiadiazolyl(2)]-N—n-butyl-N'—methyl urea | |

The production of herbicidal compositions according to the invention is carried out in a known manner by the intimate mixing and grinding of the active substances of formula I with suitable carriers, optionally with the addition of dispersion agents or solvents which are inert to the active substances. The active substances can be used for the production of dusts, sprinkling agents, granulates, coated granules, impregnated granules, homogeneous granules, wettable powders, pastes, emulsions, aerosols and solutions.

To produce the solid forms for application (dusts, sprinkling agents, granulates), the active substances are mixed with solid carriers. Examples of carriers are kaolin, talcum, bole, loess, chalk, limestone, ground limestone, ataclay, dolomite, diatomaceous earth, precipitated silicic acid, alkaline earth silicates, sodium and potassium aluminium silicates (feldspar and mica), calcium and magnesium sulphates, magnesium oxide, ground synthetic plastics; fertilisers, such as ammonium sulphate, ammonium phosphate, ammonium nitrate, urea; ground vegetable products, such as cereal-flour, bark-flour, sawdust, ground nut shells, cellulose powder, residues from plant extractions; active charcoal, etc., used either alone or as mixtures.

The grain-size of the carriers is, for dusts advantageously up to about 0.1 mm, for sprinkling agents about 0.075 to 0.2 mm and for granulates from 0.2 mm upwards.

The concentrations of active substances in the solid preparations are 0.5 to 80%, calculated on the weight of the latter.

To these mixtures additives can also be added which stabilise the active substance and/or non-ionic, anion-active and cation-active substances, which for example improve the adhesiveness of the active substances on plants and parts of plants (adhesives) and/or ensure better wettability (wetting agents) and also dispersibility (dispersing agents). The following are examples of adhesives: olein-mixture, cellulose derivatives (methyl cellulose, carboxymethyl cellulose), hydroxyethyl-glycol ethers of mono- and dialkyl-phenols having 5-15 ethylene oxide radicals per molecule and 8-9 carbon atoms in the alkyl radical, lignin-sulphonic acids, the alkali and alkaline earth metal salts thereof, polyethyleneglycol ethers, fatty alcohol polyethyleneglycol ethers having 5-20 ethylene oxide radicals per molecule and 8-18 carbon atoms in the fatty alcohol part, condensation products of ethylene oxide, propylene oxide, polyvinylpyrrolidones, polyvinyl alcohols, condensation products of urea-formaldehyde as well as latex products.

Active substance concentrates dispersible in water, i.e. wettable powders, pastes and emulsion concentrates, are compositions which can be diluted with water to give any desired concentration. They consist of active substance, carrier, optionally additives which stabilise the active substance, surface-active substances and anti-foaming agents and, optionally solvents.

The concentration of active substance in these compositions is 5-80%, calculated on the weight of the composition.

Wettable powders and pastes are obtained by mixing and grinding the active substances with dispersing agents and pulverulent carriers in suitable devices until a homogeneous mixture is obtained. Carriers which can be employed are for example those mentioned above for solid preparations. In some cases it is advantageous to use mixtures of different carriers. The following can be used for example as dispersing agents: condensation products of sulphonated naphthalene and sulphonated naphthalene derivatives with formaldehyde, condensation products of naphthalene or naphthalene sulphonic acids with phenol and formaldehyde, also alkali, ammonium and alkaline earth metal salts of lignin sulphonic acid, and also alkylaryl sulphonates, alkali and alkaline earth metal salts of dibutyl naphthalene sulphonic acid, fatty alcohol sulphates, salts of sulphated fatty alcohol glycol ether, sodium oleoylethionate, sodium oleoyl-methyltauride, ditertiary acetylene glycols, dialkyl dilauryl ammonium chloride and fatty acid alkali and alkaline earth metal salts. Suitable as anti-foaming agents are for examples silicones.

The active substances are mixed, ground, sieved and strained with the above mentioned additives in such a way that the grain-size of the solid material does not exceed 0.02-0.04 mm in the case of the wettable powders and 0.03 mm in the case of pastes. To produce the emulsion concentrates and pastes, dispersing agents, such as those described in the previous sections, organic solvents and water are used. Suitable solvents are, e.g. alcohols, benzenes, xylenes, toluene, dimethyl sulphoxide and mineral oil fractions having a boiling point between 120° and 350°. The solvents must be practically without smell, not phytotoxic, inert to the active substances and not readily inflammable.

In addition, the compositions according to the invention can be applied in the form of solutions. In this case, the active substance, or several active substances, of formula I are dissolved in suitable organic solvents, mixtures of solvents or water. Suitable for use as organic solvents are aliphatic and aromatic hydrocarbons, chlorinated derivatives thereof, alkylnaphthalene or mineral oils. The solutions contain the active substances in a concentration of between 1% and 20%, calculated on the weight of the solution.

Other biocidally active substances or agents can be mixed with the above-described compositions according to the invention. Thus the new compositions may contain, in addition to the aforesaid compounds of formula I, e.g. insecticides, other fungicides, bactericides, fungistatics, bacteriostatics or nematocides to give a wider effective range.

The compositions according to the invention can also contain plant fertilizers, trace elements, etc., The following examples serve to illustrate the forms of application of the new ureas. The term "parts" denotes parts by weight.

Granulate

The following materials are used to produce a 5% granulate:
5 parts of N-[5-trifluoromethyl-1,3,4-thiadiazolyl(2)]-N',N'-diethyl urea,
0.25 part of epichlorohydrin,
0.25 part of cetylpolyethylene glycol ether with 8 moles of ethylene oxide,
3.50 parts of polyethylene glycol (molecular weight 380-420),
91 parts of kaolin (grain size 0.3-0.8 mm).

The active substance is mixed with epichlorohydrin and dissolved in 6 parts of acetone. Polyethylene glycol and cetylpolyethyleneglycol ether are then added. The solution thus obtained is sprayed on to kaolin and then evaporated in vacuo.

Wettable powder

The following constituents are used to produce (a) a 50%, (b) a 25% and (c) a 10% wettable powder, respectively:
(a)

50 parts of N-[5-trifluoromethyl-1,3,4-thiadiazolyl(2)]-N-ethyl-N'-methyl urea,
5 parts of sodium dibutylnaphthalene sulphonate,
3 parts of naphthalene sulphonic acid/phenol sulphonic acid/formaldehyde condensate (3:2:1),
20 parts of kaolin,
22 parts of Champagne chalk;
25 parts of N-[5-trifluoromethyl-1,3,4-thiadiazolyl(2)]-N'-methyl urea,
5 parts of sodium oleylmethyltauride,
2.5 parts of naphthalene sulphonic acid/formaldehyde condensate,
0.5 part of carboxymethyl cellulose,
5 parts of neutral potassium aluminum silicate,
62 parts of kaolin;
(c)
10 parts of N-[5-trifluoromethyl-1,3,4-thiadiazolyl(2)]-N,N'-dimethyl urea,
3 parts of mixture of the sodium salts of saturated fatty alcohol sulphates (with 12 to 18 carbon atoms),
5 parts of naphthalene sulphonic acid/formaldehyde condensate,
82 parts of kaolin.

The active substance is added to the appropriate carriers (kaolin and chalk) and then mixed and ground with the additives. Wettable powders are obtained exhibiting excellent wettability and suspension properties. Suspensions of any desired concentration of active substance can be obtained from such a wettable powder by dilution with water. Such suspensions are used for controlling weeds and wild grasses in cultivated plantations.

Paste

The following materials are used to produce a 45% paste:
45 parts of N-[5-trifluoromethyl-1,3,4-thiadiazolyl(2)]-N',N'-dimethyl urea,
5 parts of sodium aluminium silicate,
14 parts of cetylpolyethylene glycol ether with 8 moles of ethylene oxide,
1 part of cetylpolyethylene glycol ethere with 5 moles of ethylene oxide,
2 parts of spindle oil,
10 parts of polyethylene glycol (molecular weight 380–420),
23 parts of water.

The active substance is intimately mixed and ground, in suitable equipment, with the additives. A paste is obtained from which suspensions of any desired concentration can be produced by dilution with water. The suspensions are suitable for the treatment of vegetable plantations.

Emulsion concentrate

The following constituents are mixed together to produce a 10% emulsion concentrate:
10 parts of N-[5-trifluoromethyl-1,3,4-thiadiazolyl(2)]N'-ethyl urea,
15 parts of oleylpolyethylene glycol ether with 8 moles of ethylene oxide,
75 parts of isophorone.

This concentrate can be diluted with water to give emulsions of required concentration. Such emulsions are suitable for controlling weeds in cultivated plantations, such as e.g. cotton, maize, etc.

The following 1,3,4-thiadiazolyl ureas are used as test compounds to determine their herbicidal activity:

1. N-[5-trifluoromethyl-1,3,4-thiadiazolyl(2)]-N'-methyl urea
2. N-[5-trifluoromethyl-1,3,4-thiadiazolyl(2)]-N',N'-dimethylurea
3. N-[5-trifluoromethyl-1,3,4-thiadiazolyl(2)]-N',N'-diethyl urea
4. N-[5-trifluoromethyl-1,3,4-thiadiazolyl(2)]-N'-isopropyl urea
5. N-[5-trifluoromethyl-1,3,4-thiadiazolyl(2)]-N'-allyl urea
6. N-[5-trifluoromethyl-1,3,4-thiadiazolyl(2)]-N-methyl-N'-cyclopropyl urea
7. N-[5-trifluoromethyl-1,3,4-thiadiazolyl(2)]-N'-cyclohexyl urea
8. N-[5-trifluoromethyl-1,3,4-thiadiazolyl(2)]-N'-methyl-N'-1-methylpropargyl urea
9. N-[5-trifluoromethyl-1,3,4-thiadiazolyl(2)]-N'-2-methoxyethyl urea
10. N-[5-trifluoromethyl-1,3,4-thiadiazolyl(2)]-N-methyl-N'-2-chloroethyl urea
11. N-[5-trifluoromethyl-1,3,4-thiadiazolyl(2)]-N-methyl-N'-n-butyl urea
12. N-[5-trifluoromethyl-1,3,4-thiadiazolyl(2)]-N,N'-dimethyl urea.

(a) Germination test
Method:
The active substance is mixed with an inert carrier (talcum) in a ratio of 1:9 and the resultant 10%-formulation is mixed with garden soil. The active substance is applied in a concentration of 0.5 g per liter of soil. The soil is filled into flower pots, and oats, ray grass, mustard and vetch are sowed therein. The results observed 20 days after sowing are expressed according to the following values:
10 = normal growth
9-1 = graduated increase in damage
0 = all plants destroyed.

(b) Contact test
Method:
Flowerpots filled with soil are sowed with oats and mustard. The active substance is applied in the form of an emulsion prepared from a 25% emulsion concentrate. The concentration is 0.5 g of active substance in 100 ml of water per m². The treatment is effected when the mustard reaches the 4–6 leaf stage. The results are observed 14 days after treatment and are expressed as above under (a).

Results of germination and contact tests

| active substance | Germination test (effect after 20 days) | | | | Contact test (effect after 14 days) | |
|---|---|---|---|---|---|---|
| | oats | ray grass | mustard | vetch | oats | mustard |
| 1 | 0 | 0 | 0 | 0 | 2 | 1 |
| 2 | 0 | 0 | 0 | 0 | 0 | 0 |
| 3 | 0 | 0 | 0 | 1 | 8 | 2 |
| 4 | 0 | 0 | 0 | 4 | 9 | 0 |
| 5 | 0 0 | 0 | 0 | 9 | 2 | |
| 6 | 0 | 0 | 0 | 0 | 6 | 1 |
| 7 | — | — | — | — | 1 (Galium)* | 0 (camomile)* |
| 8 | 1 | 0 | 0 | 0 | — | — |
| 9 | 0 | 0 | 0 | 0 | — | — |
| 10 | 1 | 1 | 0 | 0 | — | — |
| 11 | 0 | 0 | 0 | 0 | 6 | 1 |
| 12 | 0 | 0 | 0 | 0 | 0 (Galium)* | 0 |

*Used instead of oats or mustard.

We claim:
1. N-[5-Trifluoromethyl-1,3,4-thiadiazol-2-yl]-N,N'-dimethyl urea.

* * * * *